(12) United States Patent
Palushi et al.

(10) Patent No.: US 12,042,163 B2
(45) Date of Patent: Jul. 23, 2024

(54) HOLLOW TUBE SURGICAL INSTRUMENT WITH SINGLE AXIS SENSOR

(71) Applicant: Acclarent, Inc., Irvine, CA (US)

(72) Inventors: Jetmir Palushi, Irvine, CA (US); Fatemeh Akbarian, Rancho Palos Verdes, CA (US); Itzhak Fang, Irvine, CA (US); Henry F. Salazar, Pico Rivera, CA (US)

(73) Assignee: ACCLARENT, INC., Irvine, CA (US)

( * ) Notice: Subject to any disclaimer, the term of this patent is extended or adjusted under 35 U.S.C. 154(b) by 1163 days.

(21) Appl. No.: 16/553,382

(22) Filed: Aug. 28, 2019

(65) Prior Publication Data

US 2020/0107885 A1    Apr. 9, 2020

Related U.S. Application Data (60) Provisional application No. 62/741,594, filed on Oct. 5, 2018.

(51) Int. Cl.
*A61B 17/24* (2006.01)
*A61B 17/32* (2006.01)
(Continued)

(52) U.S. Cl.
CPC ...... *A61B 17/24* (2013.01); *A61B 17/320783* (2013.01); *A61B 34/20* (2016.02); *A61B 90/37* (2016.02); *A61B 17/32002* (2013.01); *A61B 2034/2051* (2016.02); *A61B 2090/3958* (2016.02); *A61B 2090/3983* (2016.02); *A61B 2217/005* (2013.01); *A61M 1/84* (2021.05)

(58) Field of Classification Search
CPC . A61B 34/20; A61B 90/37; A61B 17/320783; A61B 2034/2051; A61B 2090/3958; A61B 2090/3983; A61B 2217/005
See application file for complete search history.

(56) References Cited

U.S. PATENT DOCUMENTS 6,690,963 B2    2/2004    Ben-Haim et al.
7,720,521 B2    5/2010    Chang et al.
(Continued)

FOREIGN PATENT DOCUMENTS

JP    2018-043008 A    3/2018
JP    2018-086268 A    6/2018

OTHER PUBLICATIONS

Koulechov, Kirill. *Leistungssteuerung chirurgischer Instrumente in der kopf-chirurgie.* Diss. Technische Universität München, 2006.
(Continued)

*Primary Examiner* — John D Li
(74) *Attorney, Agent, or Firm* — Morgan, Lewis & Bockius LLP (57) ABSTRACT

An apparatus includes an elongate shaft and a position sensor. The elongate shaft defines a longitudinal axis. The elongate shaft includes a distal end, an opening, and a lumen. The position sensor is laterally offset from the longitudinal axis. The first position sensor is fixedly secured relative to the elongate shaft at a known distance from the opening. The first position sensor is configured to generate signals indicating a position of the elongate shaft in three-dimensional space.

13 Claims, 5 Drawing Sheets

(51) Int. Cl.
  *A61B 17/3207* (2006.01)
  *A61B 34/20* (2016.01)
  *A61B 90/00* (2016.01)
  *A61M 1/00* (2006.01)

(56) References Cited

U.S. PATENT DOCUMENTS

| | | | |
|---|---|---|---|
| 2004/0097805 A1* | 5/2004 | Verard | A61B 8/4254 |
| | | | 600/428 |
| 2005/0085720 A1 | 4/2005 | Jascob et al. | |
| 2006/0004286 A1* | 1/2006 | Chang | A61B 90/16 |
| | | | 606/198 |
| 2010/0249817 A1* | 9/2010 | Mark | A61B 1/313 |
| | | | 606/170 |
| 2010/0274124 A1* | 10/2010 | Jascob | A61B 5/062 |
| | | | 600/424 |
| 2011/0144633 A1 | 6/2011 | Govari | |
| 2011/0152856 A1 | 6/2011 | Govari et al. | |
| 2012/0172842 A1* | 7/2012 | Sela | A61M 25/0127 |
| | | | 604/528 |
| 2014/0081121 A1* | 3/2014 | Wilhelm | A61B 5/062 |
| | | | 600/409 |
| 2014/0288560 A1* | 9/2014 | Rubin | A61B 17/16 |
| | | | 606/180 |
| 2014/0364725 A1 | 12/2014 | Makower | |
| 2016/0008083 A1 | 1/2016 | Kesten et al. | |
| 2016/0302873 A1* | 10/2016 | Donhowe | A61B 34/10 |
| 2016/0346036 A1* | 12/2016 | Orczy-Timko | A61B 18/14 |
| 2017/0119474 A1* | 5/2017 | Kronman | A61B 90/361 |
| 2017/0189123 A1* | 7/2017 | Govari | A61B 90/13 |
| 2018/0310886 A1 | 11/2018 | Salazar et al. | |
| 2019/0038895 A1* | 2/2019 | Pianca | A61N 1/06 |
| 2019/0125391 A1 | 5/2019 | Palushi et al. | |
| 2019/0175282 A1 | 6/2019 | Akbarian et al. | |

OTHER PUBLICATIONS

International Search Report and Written Opinion dated Feb. 11, 2020 for International Application No. PCT/IB2019/058305, 15 pagers.

U.S. Appl. No. 62/775,135, entitled "Bi-Directional Articulating Surgical Shaver," filed Dec. 4, 2018.

Chinese First Office Action and Search Report dated Feb. 6, 2024, for Application No. 201980065472.6, 14 pages.

Japanese First Office Action dated Jun. 13, 2023, for Application No. 2021-518648, 6 pages.

Japanese Final Office Action dated Nov. 21, 2023, for Application No. 2021-518648, 9 pages.

* cited by examiner

HOLLOW TUBE SURGICAL INSTRUMENT WITH SINGLE AXIS SENSOR

PRIORITY

This application claims priority to U.S. Provisional Pat. App. No. 62/741,594, entitled "Hollow Tube Surgical Instrument with Single Axis Sensor," filed Oct. 5, 2018, the disclosure of which is incorporated by reference herein in its entirety.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, California. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

Surgical cutting instruments configured for removal of lesions, polyps and fibroids within the nasal cavity or other procedure areas may include an elongated inner member rotatably coaxially disposed within a tubular outer member. The distal end of the outer member may include an opening, and the distal end of the inner member may include corresponding cutting edges. Position and orientation of the cutting edges are important for the success of a procedure, so an IGS navigation system may also be particularly useful in procedures involving surgical cutting instruments being used in procedure areas of limited visibility, such as within the nasal cavity of a patient. Even where IGS navigation systems are used with medical instruments such as surgical cutting instruments, there is still a possibility of error that could impact a procedure outcome, whether the source is human error (e.g., an unintentional movement of the medical instrument or an intentional but erroneous movement, etc.) or equipment error (e.g., obscurement or failure of an endoscopic view, failure of a display of an IGS navigation system, etc.). Thus, it may be advantageous to provide an IGS navigation system with additional safety features to further reduce the risks associated with surgical procedures.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Exemplary Image Guided Surgery Navigation System

Figure 1:
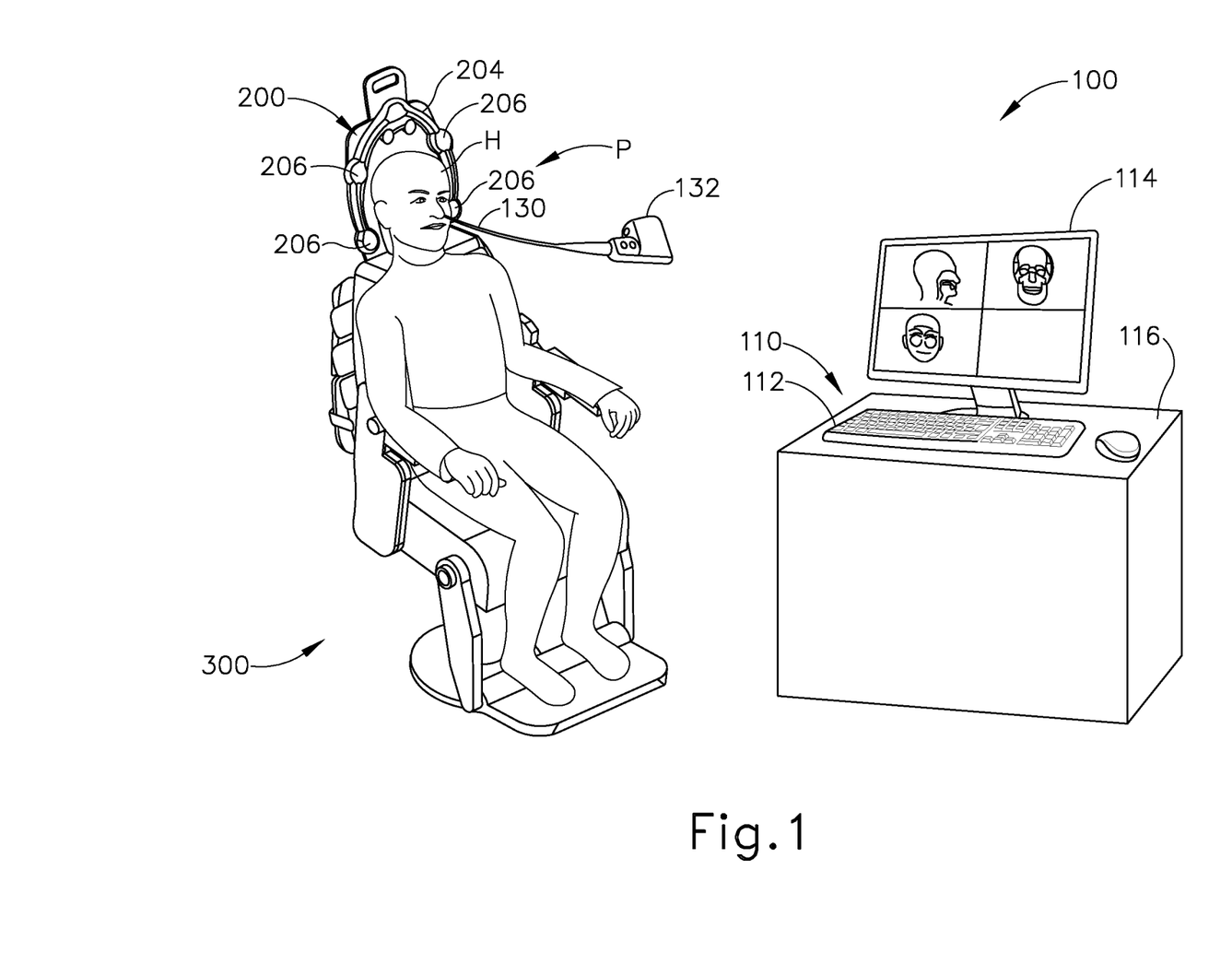
FIG. 1 depicts a schematic view of an exemplary surgery navigation system being used on a patient seated in an exemplary medical procedure chair.

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (100) enabling an ENT procedure to be performed using image guidance. In some instances, IGS navigation system (100) is used during a surgical procedure involving the use of a surgical cutting device to shave or debride tissue in or near a patient's sinuses or elsewhere within the patient's nasal cavity. In addition to or in lieu of having the components and operability described herein, IGS navigation system (100) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein in its entirety; and/or U.S. Pat. Pub. No. 2014/0364725, entitled "Systems and Methods for Performing Image Guided Procedures within the Ear, Nose, Throat and Paranasal Sinuses," published Dec. 11, 2014 (now abandoned), the disclosure of which is incorporated by reference herein in its entirety.

IGS navigation system (100) of the present example comprises a field generator assembly (200), which comprises set of magnetic field generators (206) that are integrated into a horseshoe-shaped frame (204). Field generators (206) are operable to generate alternating magnetic fields of different frequencies around the head (H) of the patient (P). A navigation guidewire (130) is inserted into the head (H) of the patient (P) in this example. Navigation guidewire (130) may be a standalone device or may be positioned on an end effector or other location of a medical instrument such as a surgical cutting instrument or dilation instrument. In the present example, frame (204) is mounted to a chair (300), with the patient (P) being seated in the chair (300) such that frame (204) is located adjacent to the head (H) of the patient (P). By way of example only, chair (300) and/or field generator assembly (200) may be configured and operable in accordance with at least some of the teachings of U.S. Pub. No. 2018/0310886, entitled "Apparatus to Secure Field Generating Device to Chair," published Nov. 1, 2018, the disclosure of which is incorporated by reference herein in its entirety.

IGS navigation system (100) of the present example further comprises a processor (110), which controls field generators (206) and other elements of IGS navigation system (100). For instance, processor (110) is operable to drive field generators (206) to generate alternating electromagnetic fields; and process signals from navigation guidewire (130) to determine the location of a sensor in navigation guidewire (130) within the head (H) of the patient (P). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

Navigation guidewire (130) includes a sensor (not shown) that is responsive to positioning within the alternating magnetic fields generated by field generators (206). A coupling unit (132) is secured to the proximal end of navigation guidewire (130) and is configured to provide communication of data and other signals between console (116) and navigation guidewire (130). Coupling unit (132) may provide wired or wireless communication of data and other signals.

In the present example, the sensor of navigation guidewire (130) comprises at least one coil at the distal end of navigation guidewire (130). When such a coil is positioned within an alternating electromagnetic field generated by field generators (206), the alternating magnetic field may generate electrical current in the coil, and this electrical current may be communicated along the electrical conduit(s) in navigation guidewire (130) and further to processor (110) via coupling unit (132). This phenomenon may enable IGS navigation system (100) to determine the location of the distal end of navigation guidewire (130) or other medical instrument (e.g., dilation instrument, surgical cutting instrument, etc.) within a three-dimensional space (i.e., within the head (H) of the patient (P), etc.). To accomplish this, processor (110) executes an algorithm to calculate location coordinates of the distal end of navigation guidewire (130) from the position related signals of the coil(s) in navigation guidewire (130). While the position sensor is located in guidewire (130) in this example, such a position sensor may be integrated into various other kinds of instruments. By way of example only, one or more position sensors may be integrated into a surgical cutting instrument (10), as will be described in greater detail below.

Processor (110) uses software stored in a memory of processor (110) to calibrate and operate IGS navigation system (100). Such operation includes driving field generators (206), processing data from navigation guidewire (130), processing data from operating controls (112), and driving display screen (114). In some implementations, operation may also include monitoring and enforcement of one or more safety features or functions of IGS navigation system (100). Processor (110) is further operable to provide video in real time via display screen (114), showing the position of the distal end of navigation guidewire (130) in relation to a video camera image of the patient's head (H), a CT scan image of the patient's head (H), and/or a computer generated three-dimensional model of the anatomy within and adjacent to the patient's nasal cavity. Display screen (114) may display such images simultaneously and/or superimposed on each other during the surgical procedure. Such displayed images may also include graphical representations of instruments that are inserted in the patient's head (H), such as navigation guidewire (130), such that the operator may view the virtual rendering of the instrument at its actual location in real time. By way of example only, display screen (114) may provide images in accordance with at least some of the teachings of U.S. Pub. No. 2016/0008083, entitled "Guidewire Navigation for Sinuplasty," published Jan. 14, 2016, the disclosure of which is incorporated by reference herein in its entirety. In the event that the operator is also using an endoscope, the endoscopic image may also be provided on display screen (114).

The images provided through display screen (114) may help guide the operator in maneuvering and otherwise manipulating instruments within the patient's head (H). It should also be understood that other components of surgical cutting instrument (10), described below, may incorporate a sensor like the sensor of navigation guidewire (130), including but not limited to shaft assembly (16).

II. Exemplary Surgical Cutting Instrument

Figure 2:
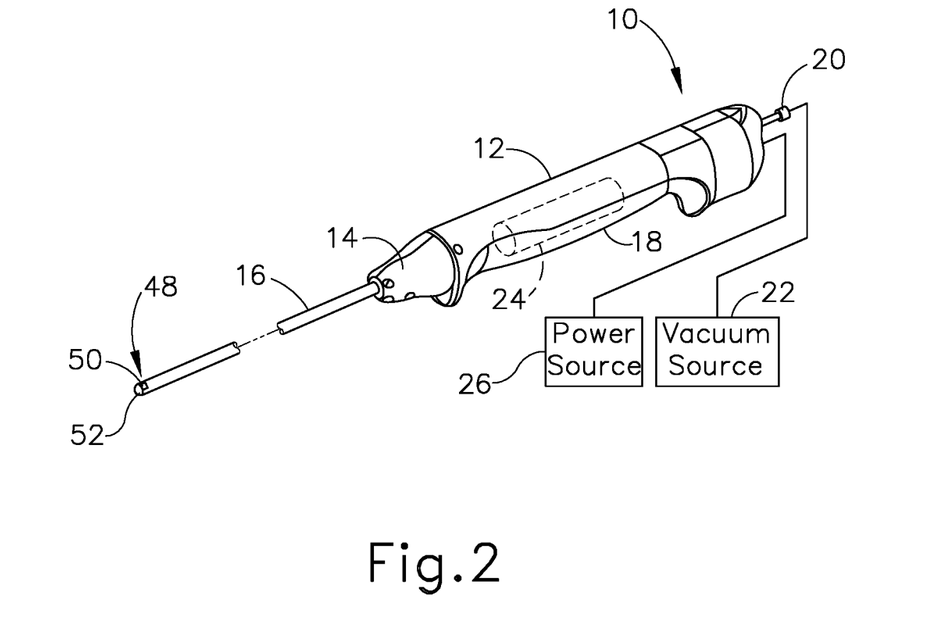
FIG. 2 depicts a perspective view of an exemplary surgical cutting instrument having a handle assembly and a first shaft assembly.
Figure 3:
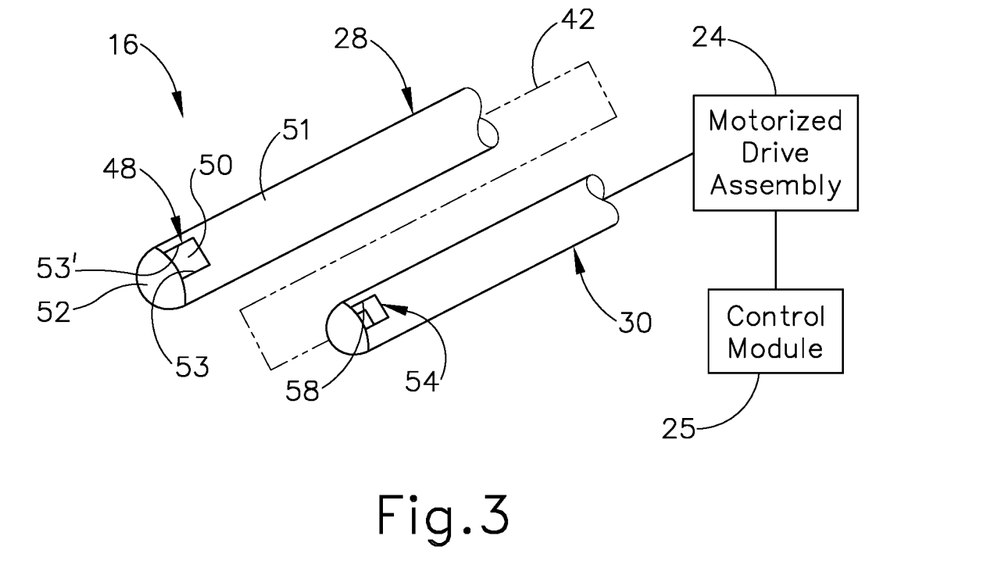
FIG. 3 depicts an exploded perspective fragmentary view of the shaft assembly of FIG. 2 having a shaft and a cutting member.

FIGS. 2-3 show a surgical cutting instrument (10) that may be used to remove tissue, such as bone tissue, from the nasal cavity, as well as from any other suitable location. Surgical cutting instrument (10) may be used in conjunction with an IGS navigation system such as IGS navigation system (100). Examples of how surgical cutting instrument (10) may incorporate one or more position sensors, to enable use with IGS navigation system (100), will be described in greater detail below. Surgical cutting instrument (10) of the present example includes a handle assembly (12), a hub (14), and a first shaft assembly (16) extending distally from handle assembly (12). Handle assembly (12) has a handle (18) which may be of any suitable configuration. Handle (18) may include controls for the operation of surgical cutting instrument (10), or the controls may be located remotely. Surgical cutting instrument (10) further includes a suction port (20) operatively connected to a vacuum source (22) and configured to enable aspiration of tissue, such as a bone tissue, from a surgical site. Rotational motion is delivered to shaft assembly (16) by a motorized drive assembly (24) within handle assembly (12) in the present example. A power source (26) connects to motorized drive assembly (24) to power surgical cutting instrument (10) for use.

Shaft assembly (16) generally includes an outer shaft (28) and an inner cutting member (30) collectively configured to receive and remove tissue from the surgical site. Cutting member (30), which is illustrated as a tube, is disposed within a longitudinally extending lumen (32) of shaft (28). Cutting member (30) is configured to be rotated about a longitudinal axis (42) of shaft assembly (16) at a distal portion. Outer shaft (28) remains rotationally stationary as cutting member (30) rotates about longitudinal axis (42). Although shaft assembly (16) is depicted as rigid, all or a portion of shaft assembly (16) may be flexible. Cutting member (30) defines a lumen and extends proximally to handle assembly (12) and connects to motorized drive assembly (24), which rotatably drives cutting member (30) relative to shaft (28).

Shaft (28) includes a window region (48) having a shaft window opening (50). A tubular sidewall (51) distally terminates in a generally hemispherical end (52). Shaft window opening (50) extends through tubular sidewall (51) of shaft (28) into central lumen (40) and is in fluid communication with the environment surrounding shaft (28). Shaft window opening (50) faces radially outwardly relative to longitudinal axis (42) such that tissue may be radially received through shaft window opening (50) into central lumen (40) in a radially inward direction. Shaft window opening (50) is surrounded by a relatively dull edge (53) in the present example. In some other versions, edge (53) is sharp.

Cutting member (30) includes a cutting window opening (54) at distal portion of cutting member (30). Cutting member (30) is hollow and thus defines an inner lumen that is in fluid communication with opening (54). Cutting window opening (54) is configured to longitudinally align with shaft window opening (50) and includes a cutting edge (58) extending therealong. At least a portion of cutting edge (58) is disposed to move adjacent to and across at least a portion of window region (48) when cutting member (30) is rotated or oscillated about longitudinal axis (42). By way of example, as cutting member (30) moves in a clockwise direction, edge (53) of window region (48) provides an opposing surface to cutting edge (58) whereby tissue may be severed to remove a cut tissue portion therefrom. In other words, edges (53, 58) may cooperate to provide a shearing action that severs tissue protruding through openings (50, 54).

With continued reference to FIGS. 2-3, vacuum source (22) generates suction through the inner lumen of cutting member (30) in a proximal direction along longitudinal axis (42) toward suction port (20). Once tissue is respectively introduced into window opening (54), suction effectively draws tissue into window opening (54) for resection while tissue blocks airflow along lumen. By way of example only, airflow through the lumen of cutting member (30), and aspiration vents for improving such airflow, may be provided in accordance with at least some of the teachings of U.S. Pub. No. 2019/0125391, entitled "Tissue Shaving Instrument," published May 2, 2019, the disclosure of which is incorporated by reference herein in its entirety.

Control module (25) may be contained with handle assembly (12) and is electrically connected to motorized drive assembly (24), which drives rotation of inner cutting member (30). Based on signals from controls of the surgical cutting instrument (10), signals from IGS navigation system (100), or signals from another device, sensor, or source, control module (25) thereby directs rotation of inner cutting member (30) to either cease driving rotation of inner cutting member (30) or simply prevent rotation regardless of input provided by the operator.

III. Integration of Position Sensors in Shaving Instrument

As noted above, it may be desirable to have information regarding the position of an instrument within a head (H) of a patient (P). As also noted above, IGS navigation system (100) may provide such information, by providing video in real time via display screen (114), showing the position of the distal end of an instrument (e.g., navigation guidewire (130)) in relation to an image of anatomy within the patient's head (H). In procedures where an instrument like surgical cutting instrument (10) is used, it may be beneficial to provide a physician with information indicating the position and orientation of shaft window opening (50), in addition to providing information indicating the position of the distal end of shaft assembly (16) in general. This may enable the physician to position shaft window opening (50) more precisely in relation to tissue/bone/etc. that the physician wishes to remove with cutting instrument. To accomplish this, shaft assembly (16) may be modified to incorporate one or more position sensors like the position sensor of guidewire (130) described above. Some examples of how a shaving instrument may incorporate a position sensor are described in U.S. Pub. No. 2019/0175282, entitled "Tissue Shaving Instrument with Navigation Sensor," published Jun. 13, 2019, the disclosure of which is incorporated by reference herein in its entirety. The following describes various other examples of ways in which a shaft assembly (16) of a surgical cutting instrument (10) may incorporate one or more position sensors to communicate with IGS navigation system (100).

While the following examples are provided in the context of a surgical cutting instrument (10), the following teachings may be readily applied to various other kinds of instruments. By way of example only, one or more position sensors may be incorporated into a suction instrument and/or various other kinds of instruments in accordance with the teachings below. Various suitable ways in which the following teachings may be applied to suction instruments and/or other kinds of instruments will be apparent to those skilled in the art.

A. Exemplary Cutting Instrument Shaft with Single Offset Position Sensor

Figure 4:
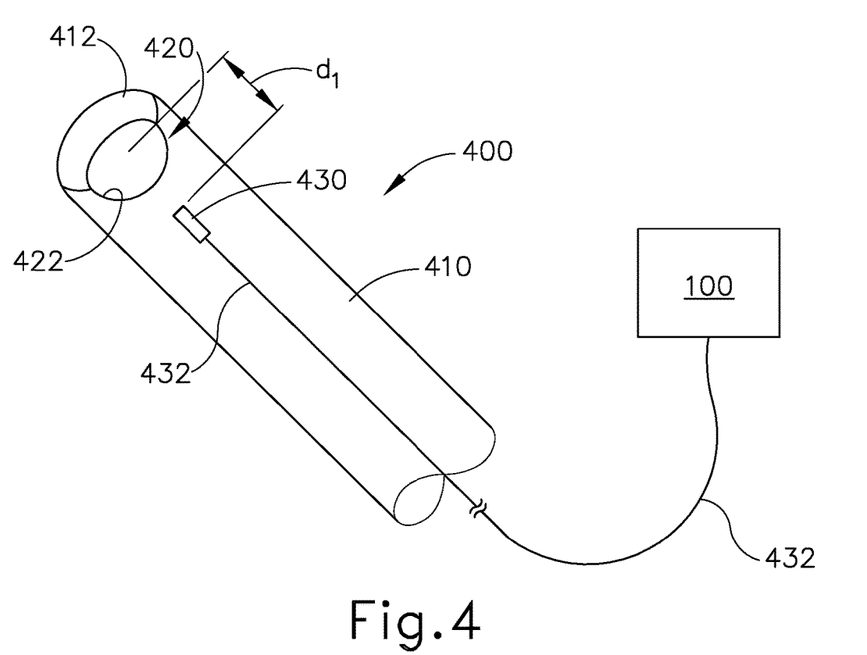
FIG. 4 depicts a perspective view of a distal portion of an exemplary alternative outer shaft that may be incorporated into the shaft assembly of FIG. 2.
Figure 5:
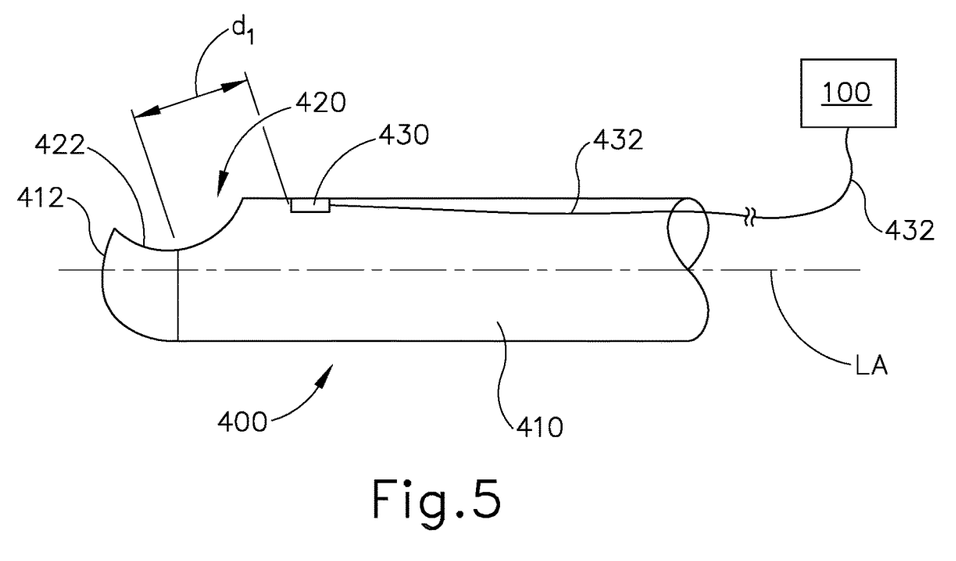
FIG. 5 depicts a side elevational view of the distal portion of the outer shaft of FIG. 4.

FIGS. 4-5 show an exemplary alternative outer shaft (400) that may be incorporated into shaft assembly (16) in place of outer shaft (28). Outer shaft (400) of this example may be configured and operable just like outer shaft (28), except for the differences explicitly discussed below. Outer shaft (400) of this example includes a cylindraceous body (410) with a rounded distal end (412). A laterally oriented window opening (420) is formed just proximal to distal end (412). Opening (420) is defined by an edge (422). In some versions, at least a portion of edge (422) is sharp.

Outer shaft (400) is configured to receive cutting member (30) and is configured to be fixedly secured relative to handle assembly (12). Opening (420) is sized and positioned to correspond with the size and position of window opening (54) of cutting member (30). Drive assembly (24) may drive cutting member (30) to rotate within outer shaft (400). Vacuum source (22) may be activated to assist in drawing tissue into openings (54, 420); and edges (58, 422) may cooperate to shear tissue, etc. that is drawn into openings (54, 420) as cutting member (30) is rotated within outer shaft (400).

Unlike outer shaft (28), outer shaft (400) of the present example includes a position sensor (430). Position sensor (430) is located near distal end (412) of outer shaft (400), proximal to opening (420). The location of position sensor (430) is at a fixed distance ($d_1$) from the center of opening (420) in the present example. In this context, the term "fixed" is simply meant to indicate that position sensor (430) does not move relative to body (410) after the manufacturing process is complete, such that the distance ($d_1$) does not change during operation of the surgical cutting instrument. In some versions, the distance ($d_1$) is predetermined. In some other versions, the distance ($d_1$) is not predetermined and may vary slightly from one surgical cutting instrument to another surgical cutting instrument, such as may be expected from manufacturing tolerances. In such scenarios, a given surgical cutting instrument may be calibrated after the manufacturing process is complete, before the surgical cutting instrument is used in a medical procedure. Such a calibration process may be used to determine the precise values of the distance ($d_1$) for the particular surgical cutting instrument at hand. Various suitable ways in which such a calibration process may be carried out will be apparent to those skilled in the art in view of the teachings herein.

The information gathered during the above-described calibration process, including (but not necessarily limited to) the precise values of the distance ($d_1$) may be stored on a local memory device contained within the surgical cutting instrument itself. By way of example only, a handle assembly (12) (or some other component) may include an EEPROM on which the calibration information is stored. Alternatively, any other suitable kind of storage device may be used in any other suitable location. At the beginning of a medical procedure, processor (110) may interrogate the storage device to retrieve the calibration data from the surgical cutting instrument at hand; and may take this data into account when processing signals from position sensor (430) to ensure that the position data presented to the physician is as accurate as possible. Regardless of whether the distance ($d_1$) for the particular surgical cutting instrument at hand was predetermined or determined through a calibration process, the distance ($d_1$) for the particular surgical cutting instrument at hand may be "known" by the processor (110) before the physician performs the medical procedure with the surgical cutting instrument.

Position sensor (430) may comprise a coil that is configured to generate electrical current in response to an alternating electromagnetic field generated by field generators (206), such that position sensor (430) may generate electrical signals that are indicative of the position of distal end (412) of outer shaft (400) within the head (H) of the patient (P). Moreover, since the location of position sensor (430) is at a fixed distance ($d_1$) from the center of opening (420), signals from position sensor (430) may also indicate the position of the center of opening (420) within the head (H) of the patient (P).

With processor (110) having information from position sensor (430) indicating the position of the center of opening (420) within the head (H) of the patient (P), processor (110) may drive display (114) to depict the position of the center of opening (420) in relation to an image of anatomy within the head (H) of the patient (P), in real time, as distal end (412) is moved within the head (H) of the patient (P). Moreover, since the dimensions and configuration of opening (420) are predetermined, and since processor (110) will have data indicating the position of the center of opening (420) within the head (H) of the patient (P), processor (110) may drive display (114) to depict a graphical representation of opening (420) to more clearly and precisely indicate the position of opening (420) within the head (H) of the patient (P).

In the present example, position sensor (430) is laterally offset from the central longitudinal axis (LA) of body (410). Thus, as outer shaft (400) is rotated about the central longitudinal axis (LA) of body (410) (e.g., as the operator grasping handle assembly (12) rotates the entire instrument (10)), position sensor (430) will sense such movement and thereby provide signals indicating the angular position of outer shaft (400) about the central longitudinal axis (LA) of body (410). In other words, position sensor (430) will indicate the roll orientation or angular position of opening (420) about the central longitudinal axis (LA) of body (410). Processor (110) may thus drive display (114) to indicate the roll orientation or angular position of opening (420), in addition to indicating the three-dimensional position of opening (420), within the head of the patient. In such a rendering, processor (110) may drive display (114) to render the shape of outer shaft (400) and the shape of opening (420), with enhanced indication of the location of opening (420).

As noted above, position sensor (430) may take the form of a coil, where a wire is wound about a coil axis. In the present example, the coil axis of position sensor (430) is parallel with the central longitudinal axis (LA) of body (410). Alternatively, the coil axis of position sensor (430)

may have any other suitable relationship with the central longitudinal axis (LA) of body (410).

Position sensor (430) is positioned on or in body (410) in such a way as to not interfere with movement of cutting member (30) within outer shaft (400). By way of example only, position sensor (430) may be closely secured to the inner diameter of body (410). As another merely illustrative example, position sensor (430) may be integrated directly into the sidewall of body (410). As yet another merely illustrative example, position sensor (430) may be closely secured to the outer diameter of body (410). Other suitable ways in which position sensor (430) may be fixedly integrated on or in body (410) will be apparent to those skilled in the art in view of the teachings herein.

Position sensor (430) is in communication with IGS navigation system (100) via at least one electrical conduit (432). By way of example only, electrical conduit (432) may comprise one or more wires running along at least a portion of the length of body (410). In addition, or in the alternative, electrical conduit (432) may include one or more electrical traces formed on or in body (410). Other suitable forms that electrical conduit (432) may take will be apparent to those skilled in the art in view of the teachings herein. In some versions, electrical conduit (432) is directly coupled with processor (110) via a wired communication. In some other versions, electrical conduit (432) is wirelessly coupled with processor (110), such as by a coupling unit (132) or other wireless communication device.

B. Exemplary Cutting Instrument Shaft with Pair of Offset Position Sensors

Figure 6:
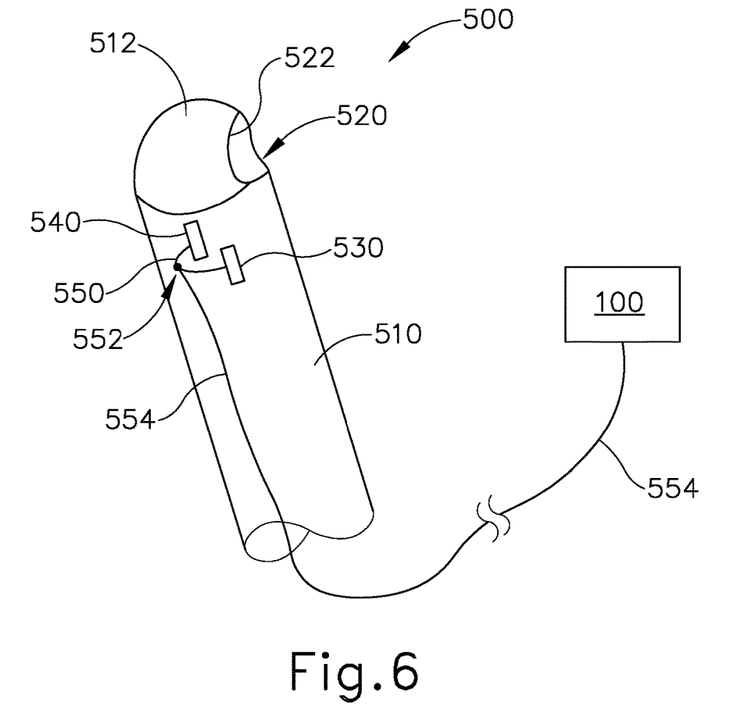
FIG. 6 depicts a perspective view of a distal portion of another exemplary alternative outer shaft that may be incorporated into the shaft assembly of FIG. 2.
Figure 7:
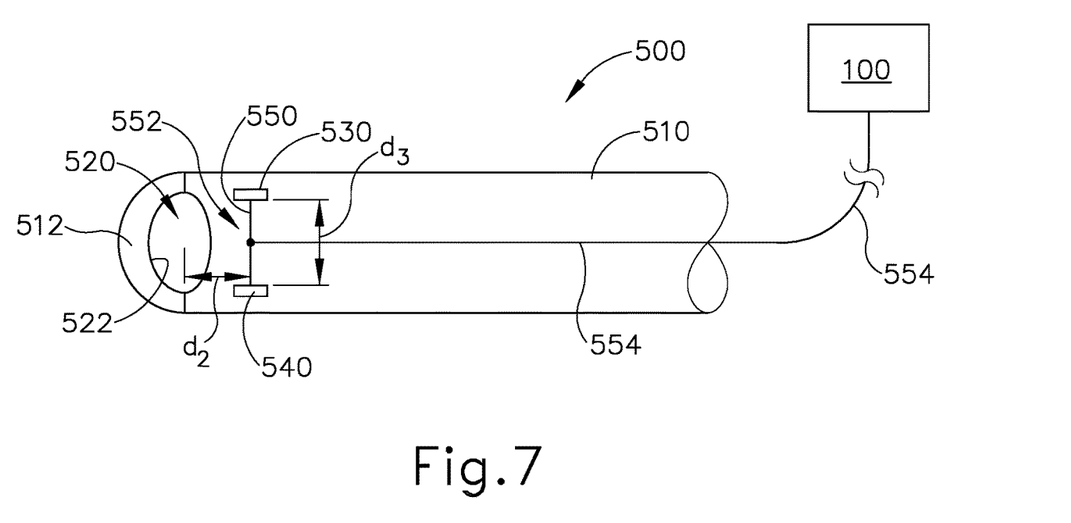
FIG. 7 depicts a top plan view of the distal portion of the outer shaft of FIG. 6.

FIGS. 6-7 show another exemplary alternative outer shaft (500) that may be incorporated into shaft assembly (16) in place of outer shaft (28). Outer shaft (500) of this example may be configured and operable just like outer shaft (28), except for the differences explicitly discussed below. Outer shaft (500) of this example includes a cylindraceous body (510) with a rounded distal end (512). A laterally oriented window opening (520) is formed just proximal to distal end (512). Opening (520) is defined by an edge (522). In some versions, at least a portion of edge (522) is sharp.

Outer shaft (500) is configured to receive cutting member (30) and is configured to be fixedly secured relative to handle assembly (12). Opening (520) is sized and positioned to correspond with the size and position of window opening (54) of cutting member (30). Drive assembly (24) may drive cutting member (30) to rotate within outer shaft (500). Vacuum source (22) may be activated to assist in drawing tissue into openings (54, 520); and edges (58, 522) may cooperate to shear tissue, etc. that is drawn into openings (54, 520) as cutting member (30) is rotated within outer shaft (500).

Unlike outer shaft (28), outer shaft (500) of the present example includes a pair of position sensors (530, 540). Position sensors (530, 540) are located near distal end (512) of outer shaft (500), proximal to opening (520). Position sensors (530, 540) are laterally offset from each other but are at the same longitudinal position in this example, though this is merely optional. Position sensors (530, 540) are coupled with a node (552) via a conduit (550), which extends circumferentially along the sidewall of body (510). Another conduit (554) is also coupled with node (552). Conduit (554) is further coupled with IGS navigation system (100).

The locations of position sensors (530, 540) are fixed relative to body (510) in the present example. Thus, the distance ($d_2$) between node (552) and the center of opening (520) is fixed in the present example. Similarly, the distance ($d_3$) between position sensors (530, 540) is fixed in the present example. In this context, the term "fixed" is simply meant to indicate that position sensors (530, 540) do not move relative to body (510) after the manufacturing process is complete, such that the distances ($d_2$, $d_3$) do not change during operation of the surgical cutting instrument. In some versions, the distances ($d_2$, $d_3$) are predetermined. In some other versions, the distances ($d_2$, $d_3$) are not predetermined and may vary slightly from one surgical cutting instrument to another surgical cutting instrument, such as may be expected from manufacturing tolerances. In such scenarios, a given surgical cutting instrument may be calibrated after the manufacturing process is complete, before the surgical cutting instrument is used in a medical procedure. Such a calibration process may be used to determine the precise values of the distances ($d_2$, $d_3$) for the particular surgical cutting instrument at hand. Various suitable ways in which such a calibration process may be carried out will be apparent to those skilled in the art in view of the teachings herein.

The information gathered during the above-described calibration process, including (but not necessarily limited to) the precise values of the distances ($d_2$, $d_3$) may be stored on a local memory device contained within the surgical cutting instrument itself. By way of example only, a handle assembly (12) (or some other component) may include an EEPROM on which the calibration information is stored. Alternatively, any other suitable kind of storage device may be used in any other suitable location. At the beginning of a medical procedure, processor (110) may interrogate the storage device to retrieve the calibration data from the surgical cutting instrument at hand; and may take this data into account when processing signals from position sensors (530, 540) to ensure that the position data presented to the physician is as accurate as possible. Regardless of whether the distances ($d_2$, $d_3$) for the particular surgical cutting instrument at hand was predetermined or determined through a calibration process, the distances ($d_2$, $d_3$) for the particular surgical cutting instrument at hand may be "known" by the processor (110) before the physician performs the medical procedure with the surgical cutting instrument.

Each position sensor (530, 540) may comprise a coil that is configured to generate electrical current in response to an alternating electromagnetic field generated by field generators (206), such that position sensors (530, 540) may generate electrical signals that are indicative of the position of distal end (512) of outer shaft (500) within the head (H) of the patient (P). Since the positioning of sensors (530, 540) relative to the center of opening (520) is known, signals from position sensors (530, 540) may also indicate the position of the center of opening (520) within the head (H) of the patient (P).

With processor (110) having information from position sensors (530, 540) indicating the position of the center of opening (520) within the head (H) of the patient (P), processor (110) may drive display (114) to depict the position of the center of opening (520) in relation to an image of anatomy within the head (H) of the patient (P), in real time, as distal end (512) is moved within the head (H) of the patient (P). Moreover, since the dimensions and configuration of opening (520) are predetermined, and since processor (110) will have data indicating the position of the center of opening (520) within the head (H) of the patient (P), processor (110) may drive display (114) to depict a graphical representation of opening (520) to more clearly and precisely indicate the position of opening (520) within the head (H) of the patient (P).

In the present example, position sensors (530, 540) are laterally offset from the central longitudinal axis of body (510). Thus, as outer shaft (500) is rotated about the central longitudinal axis of body (510) (e.g., as the operator grasping handle assembly (12) rotates the entire instrument (10)), position sensors (530, 540) will sense such movement and thereby provide signals indicating the angular position of outer shaft (500) about the central longitudinal axis of body (510). In other words, position sensors (530, 540) will indicate the roll orientation or angular position of opening (520) about the central longitudinal axis of body (510). Processor (110) may thus drive display (114) to indicate the roll orientation or angular position of opening (520), in addition to indicating the three-dimensional position of opening (520), within the head of the patient. In such a rendering, processor (110) may drive display (114) to render the shape of outer shaft (500) and the shape of opening (520), with enhanced indication of the location of opening (520).

As noted above, each position sensor (530, 540) may take the form of a coil, where a wire is wound about a coil axis. In the present example, the coil axis of each position sensor (530, 540) is parallel with the central longitudinal axis of body (510). Alternatively, the coil axis of each position sensor (530) may have any other suitable relationship with the central longitudinal axis of body (510).

Each position sensor (530, 540) is positioned on or in body (510) in such a way as to not interfere with movement of cutting member (30) within outer shaft (500). By way of example only, each position sensor (530, 540) may be closely secured to the inner diameter of body (510). As another merely illustrative example, each position sensor (530, 540) may be integrated directly into the sidewall of body (510). As yet another merely illustrative example, each position sensor (530, 540) may be closely secured to the outer diameter of body (510). Other suitable ways in which position sensors (530, 540) may be fixedly integrated on or in body (510) will be apparent to those skilled in the art in view of the teachings herein.

Position sensors (530, 540) are in communication with IGS navigation system (100) via electrical conduits (550, 554). By way of example only, electrical conduits (550, 554) may comprise one or more wires running along at least a portion of the length of body (510). In addition, or in the alternative, electrical conduits (550, 554) may include one or more electrical traces formed on or in body (510). Other suitable forms that electrical conduits (550, 554) may take will be apparent to those skilled in the art in view of the teachings herein. In some versions, electrical conduit (554) is directly coupled with processor (110) via a wired communication. In some other versions, electrical conduit (554) is wirelessly coupled with processor (110), such as by a coupling unit (132) or other wireless communication device.

C. Exemplary Cutting Instrument Shaft with Perpendicular Position Sensors

Figure 8:
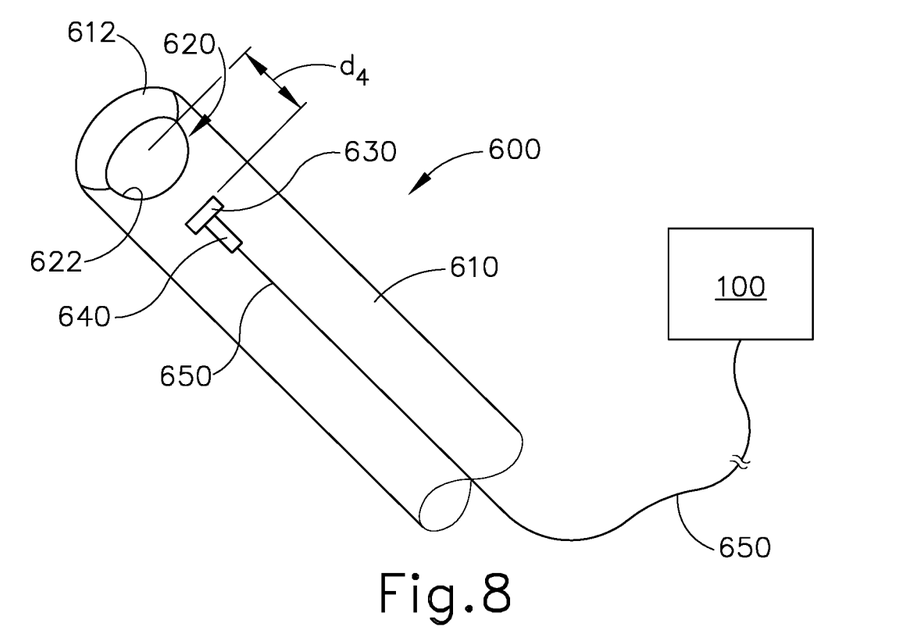
FIG. 8 depicts a perspective view of a distal portion of another exemplary alternative outer shaft that may be incorporated into the shaft assembly of FIG. 2.

FIG. 8 shows another exemplary alternative outer shaft (600) that may be incorporated into shaft assembly (16) in place of outer shaft (28). Outer shaft (600) of this example may be configured and operable just like outer shaft (28), except for the differences explicitly discussed below. Outer shaft (600) of this example includes a cylindraceous body (610) with a rounded distal end (612). A laterally oriented window opening (620) is formed just proximal to distal end (612). Opening (620) is defined by an edge (622). In some versions, at least a portion of edge (622) is sharp.

Outer shaft (600) is configured to receive cutting member (30) and is configured to be fixedly secured relative to handle assembly (12). Opening (620) is sized and positioned to correspond with the size and position of window opening (54) of cutting member (30). Drive assembly (24) may drive cutting member (30) to rotate within outer shaft (600). Vacuum source (22) may be activated to assist in drawing tissue into openings (54, 620); and edges (58, 622) may cooperate to shear tissue, etc. that is drawn into openings (54, 620) as cutting member (30) is rotated within outer shaft (600).

Unlike outer shaft (28), outer shaft (600) of the present example includes a pair of position sensors (630, 640). Position sensors (630, 640) are located near distal end (612) of outer shaft (600), proximal to opening (620). Position sensors (630, 640) are oriented perpendicular to each other in the present example, with position sensor (630) being distal to position sensor (640). Both position sensors (630, 640) are coupled with an electrical conduit (650), which provides a path for communication with IGS navigation system (100) as described in greater detail below.

The locations of position sensors (630, 640) are fixed relative to body (610) in the present example. Thus, the distance ($d_4$) between position sensors (630, 640) and the center of opening (620) is fixed in the present example. In this context, the term "fixed" is simply meant to indicate that position sensors (630, 640) do not move relative to body (610) after the manufacturing process is complete, such that the distance ($d_4$) does not change during operation of the surgical cutting instrument. In some versions, the distance ($d_4$) is predetermined. In some other versions, the distance ($d_4$) is not predetermined and may vary slightly from one surgical cutting instrument to another surgical cutting instrument, such as may be expected from manufacturing tolerances. In such scenarios, a given surgical cutting instrument may be calibrated after the manufacturing process is complete, before the surgical cutting instrument is used in a medical procedure. Such a calibration process may be used to determine the precise values of the distance ($d_4$) for the particular surgical cutting instrument at hand. Various suitable ways in which such a calibration process may be carried out will be apparent to those skilled in the art in view of the teachings herein.

The information gathered during the above-described calibration process, including (but not necessarily limited to) the precise values of the distance ($d_4$) may be stored on a local memory device contained within the surgical cutting instrument itself. By way of example only, a handle assembly (12) (or some other component) may include an EEPROM on which the calibration information is stored. Alternatively, any other suitable kind of storage device may be used in any other suitable location. At the beginning of a medical procedure, processor (110) may interrogate the storage device to retrieve the calibration data from the surgical cutting instrument at hand; and may take this data into account when processing signals from position sensors (630, 640) to ensure that the position data presented to the physician is as accurate as possible. Regardless of whether the distance ($d_4$) for the particular surgical cutting instrument at hand was predetermined or determined through a calibration process, the distance ($d_4$) for the particular surgical cutting instrument at hand may be "known" by the processor (110) before the physician performs the medical procedure with the surgical cutting instrument.

Each position sensor (630, 640) may comprise a coil that is configured to generate electrical current in response to an alternating electromagnetic field generated by field generators (206), such that position sensors (630, 640) may generate electrical signals that are indicative of the position of distal end (612) of outer shaft (600) within the head (H) of the patient (P). Since the positioning of sensors (630, 640) relative to the center of opening (620) is known, signals from position sensors (630, 640) may also indicate the position of the center of opening (620) within the head (H) of the patient (P).

With processor (110) having information from position sensors (630, 640) indicating the position of the center of opening (620) within the head (H) of the patient (P), processor (110) may drive display (114) to depict the position of the center of opening (620) in relation to an image of anatomy within the head (H) of the patient (P), in real time, as distal end (612) is moved within the head (H) of the patient (P). Moreover, since the dimensions and configuration of opening (620) are predetermined, and since processor (110) will have data indicating the position of the center of opening (620) within the head (H) of the patient (P), processor (110) may drive display (114) to depict a graphical representation of opening (620) to more clearly and precisely indicate the position of opening (620) within the head (H) of the patient (P).

In the present example, position sensors (630, 640) are laterally offset from the central longitudinal axis of body (610). Thus, as outer shaft (600) is rotated about the central longitudinal axis of body (610) (e.g., as the operator grasping handle assembly (12) rotates the entire instrument (10)), position sensors (630, 640) will sense such movement and thereby provide signals indicating the angular position of outer shaft (600) about the central longitudinal axis of body (610). In other words, position sensors (630, 640) will indicate the roll orientation or angular position of opening (620) about the central longitudinal axis of body (610). Processor (110) may thus drive display (114) to indicate the roll orientation or angular position of opening (620), in addition to indicating the three-dimensional position of opening (620), within the head of the patient. In such a rendering, processor (110) may drive display (114) to render the shape of outer shaft (600) and the shape of opening (620), with enhanced indication of the location of opening (620).

As noted above, each position sensor (630, 640) may take the form of a coil, where a wire is wound about a coil axis. In the present example, the coil axis of position sensor (640) is parallel with the central longitudinal axis of body (610); while the coil axis of position sensor (630) is perpendicular to the coil axis of position sensor (640). Alternatively, the coil axis of each position sensor (630, 640) may have any other suitable relationship with the central longitudinal axis of body (610) and with each other.

Each position sensor (630, 640) is positioned on or in body (610) in such a way as to not interfere with movement of cutting member (30) within outer shaft (600). By way of example only, each position sensor (630, 640) may be closely secured to the inner diameter of body (610). As another merely illustrative example, each position sensor (630, 640) may be integrated directly into the sidewall of body (610). As yet another merely illustrative example, each position sensor (630, 640) may be closely secured to the outer diameter of body (610). Other suitable ways in which position sensors (630, 640) may be fixedly integrated on or in body (610) will be apparent to those skilled in the art in view of the teachings herein.

Position sensors (630, 640) are in communication with IGS navigation system (100) via electrical conduit (650). By way of example only, electrical conduit (650) may comprise one or more wires running along at least a portion of the length of body (610). In addition, or in the alternative, electrical conduit (650) may include one or more electrical traces formed on or in body (610). Other suitable forms that electrical conduit (650) may take will be apparent to those skilled in the art in view of the teachings herein. In some versions, electrical conduit (650) is directly coupled with processor (110) via a wired communication. In some other versions, electrical conduit (650) is wirelessly coupled with processor (110), such as by a coupling unit (132) or other wireless communication device.

D. Exemplary Cutting Instrument Shaft with Helically Arranged Position Sensors

Figure 9:
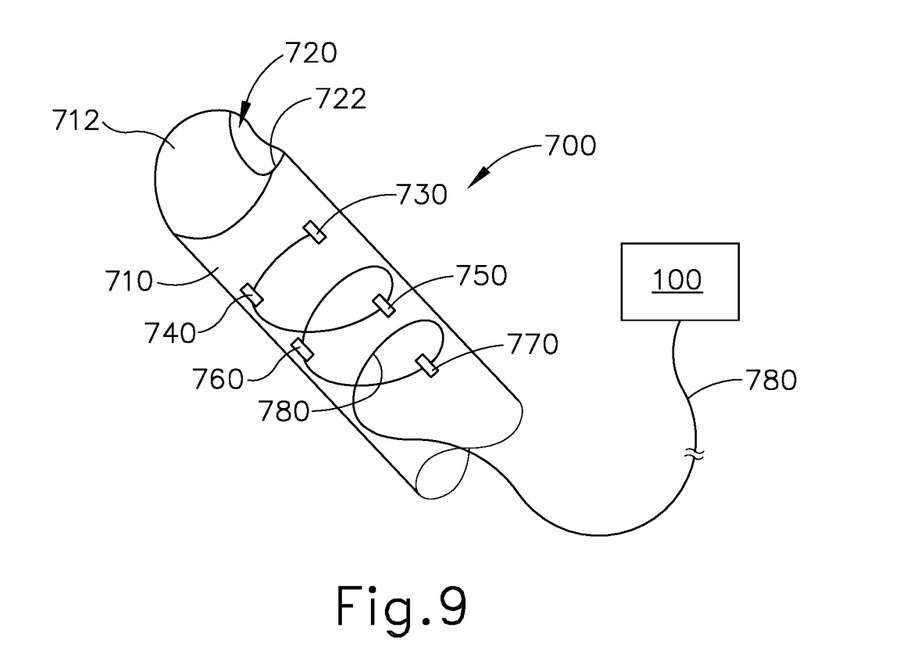
FIG. 9 depicts a perspective view of a distal portion of another exemplary alternative outer shaft that may be incorporated into the shaft assembly of FIG. 2.

FIG. 9 shows another exemplary alternative outer shaft (700) that may be incorporated into shaft assembly (16) in place of outer shaft (28). Outer shaft (700) of this example may be configured and operable just like outer shaft (28), except for the differences explicitly discussed below. Outer shaft (700) of this example includes a cylindraceous body (710) with a rounded distal end (712). A laterally oriented window opening (720) is formed just proximal to distal end (712). Opening (720) is defined by an edge (722). In some versions, at least a portion of edge (722) is sharp.

Outer shaft (700) is configured to receive cutting member (30) and is configured to be fixedly secured relative to handle assembly (12). Opening (720) is sized and positioned to correspond with the size and position of window opening (54) of cutting member (30). Drive assembly (24) may drive cutting member (30) to rotate within outer shaft (700). Vacuum source (22) may be activated to assist in drawing tissue into openings (54, 720); and edges (58, 722) may cooperate to shear tissue, etc. that is drawn into openings (54, 720) as cutting member (30) is rotated within outer shaft (700).

Unlike outer shaft (28), outer shaft (700) of the present example includes a set of position sensors (730, 740, 750, 760, 770). Position sensor (730) is located near distal end (712) of outer shaft (700), proximal to opening (720). Position sensors (740, 750, 760, 770) are proximal to position sensor (730), positioned along a helical path. Position sensors (730, 740, 750, 760, 770) are coupled with an electrical conduit (780), which provides a path for communication with IGS navigation system (100) as described in greater detail below.

The locations of position sensors (730, 740, 750, 760, 770) are fixed relative to body (710) in the present example. Thus, the distance between each position sensor (730, 740, 750, 760, 770) and the center of opening (720) is fixed in the present example. In this context, the term "fixed" is simply meant to indicate that position sensors (730, 740, 750, 760, 770) do not move relative to body (710) after the manufacturing process is complete, such that the distance between each position sensor (730, 740, 750, 760, 770) and the center of opening (720) does not change during operation of the surgical cutting instrument. In some versions, the distance between each position sensor (730, 740, 750, 760, 770) and the center of opening (720) is predetermined. In some other versions, the distance between each position sensor (730, 740, 750, 760, 770) and the center of opening (720) is not predetermined and may vary slightly from one surgical cutting instrument to another surgical cutting instrument, such as may be expected from manufacturing tolerances. In such scenarios, a given surgical cutting instrument may be calibrated after the manufacturing process is complete, before the surgical cutting instrument is used in a medical procedure. Such a calibration process may be used to determine the precise values of the distance between each position sensor (730, 740, 750, 760, 770) and the center of opening (720) for the particular surgical cutting instrument at hand. Various suitable ways in which such a calibration process may be carried out will be apparent to those skilled in the art in view of the teachings herein.

The information gathered during the above-described calibration process, including (but not necessarily limited to) the precise values of the distance between each position sensor (730, 740, 750, 760, 770) and the center of opening (720) may be stored on a local memory device contained within the surgical cutting instrument itself. By way of example only, a handle assembly (12) (or some other component) may include an EEPROM on which the calibration information is stored. Alternatively, any other suitable kind of storage device may be used in any other suitable location. At the beginning of a medical procedure, processor (110) may interrogate the storage device to retrieve the calibration data from the surgical cutting instrument at hand; and may take this data into account when processing signals from position sensors (730, 740, 750, 760, 770) to ensure that the position data presented to the physician is as accurate as possible. Regardless of whether the distance between each position sensor (730, 740, 750, 760, 770) and the center of opening (720) for the particular surgical cutting instrument at hand was predetermined or determined through a calibration process, the distance between each position sensor (730, 740, 750, 760, 770) and the center of opening (720) for the particular surgical cutting instrument at hand may be "known" by the processor (110) before the physician performs the medical procedure with the surgical cutting instrument.

Each position sensor (730, 740, 750, 760, 770) may comprise a coil that is configured to generate electrical current in response to an alternating electromagnetic field generated by field generators (206), such that position sensors (730, 740, 750, 760, 770) may generate electrical signals that are indicative of the position of distal end (712) of outer shaft (700) within the head (H) of the patient (P). Since the positioning of sensors (730, 740, 750, 760, 770) relative to the center of opening (720) is known, signals from position sensors (730, 740, 750, 760, 770) may also indicate the position of the center of opening (720) within the head (H) of the patient (P).

With processor (110) having information from position sensors (730, 740, 750, 760, 770) indicating the position of the center of opening (720) within the head (H) of the patient (P), processor (110) may drive display (114) to depict the position of the center of opening (720) in relation to an image of anatomy within the head (H) of the patient (P), in real time, as distal end (612) is moved within the head (H) of the patient (P). Moreover, since the dimensions and configuration of opening (720) are predetermined, and since processor (110) will have data indicating the position of the center of opening (720) within the head (H) of the patient (P), processor (110) may drive display (114) to depict a graphical representation of opening (720) to more clearly and precisely indicate the position of opening (720) within the head (H) of the patient (P).

In the present example, position sensors (730, 740, 750, 760, 770) are laterally offset from the central longitudinal axis of body (710). Thus, as outer shaft (700) is rotated about the central longitudinal axis of body (710) (e.g., as the operator grasping handle assembly (12) rotates the entire instrument (10)), position sensors (730, 740, 750, 760, 770) will sense such movement and thereby provide signals indicating the angular position of outer shaft (700) about the central longitudinal axis of body (710). In other words, position sensors (730, 740, 750, 760, 770) will indicate the roll orientation or angular position of opening (720) about the central longitudinal axis of body (710). Processor (110) may thus drive display (114) to indicate the roll orientation or angular position of opening (720), in addition to indicating the three-dimensional position of opening (720), within the head of the patient. In such a rendering, processor (110) may drive display (114) to render the shape of outer shaft (700) and the shape of opening (720), with enhanced indication of the location of opening (720).

As noted above, each position sensor (730, 740, 750, 760, 770) may take the form of a coil, where a wire is wound about a coil axis. In the present example, the coil axis of each position sensor (730, 740, 750, 760, 770) is parallel with the central longitudinal axis of body (710), such that the coil axes of all position sensors (730, 740, 750, 760, 770) are parallel with each other. Alternatively, the coil axis of each position sensor (730, 740, 750, 760, 770) may have any other suitable relationship with the central longitudinal axis of body (710) and with each other. While five position sensors (730, 740, 750, 760, 770) are shown in this example, outer shaft (700) may instead include any other suitable number of position sensors, including any number greater than two. The position sensors in such a plurality may be arranged along a helical path; or may otherwise be offset from each other angularly and longitudinally.

Each position sensor (730, 740, 750, 760, 770) is positioned on or in body (710) in such a way as to not interfere with movement of cutting member (30) within outer shaft (700). By way of example only, each position sensor (730, 740, 750, 760, 770) may be closely secured to the inner diameter of body (710). As another merely illustrative example, each position sensor (730, 740, 750, 760, 770) may be integrated directly into the sidewall of body (710). As yet another merely illustrative example, each position sensor (730, 740, 750, 760, 770) may be closely secured to the outer diameter of body (710). Other suitable ways in which position sensors (730, 740, 750, 760, 770) may be fixedly integrated on or in body (710) will be apparent to those skilled in the art in view of the teachings herein.

Position sensors (730, 740, 750, 760, 770) are in communication with IGS navigation system (100) via electrical conduit (780). By way of example only, electrical conduit (780) may comprise one or more wires running along at least a portion of the length of body (710). In addition, or in the alternative, electrical conduit (780) may include one or more electrical traces formed on or in body (710). Other suitable forms that electrical conduit (780) may take will be apparent to those skilled in the art in view of the teachings herein. In some versions, electrical conduit (780) is directly coupled with processor (110) via a wired communication. In some other versions, electrical conduit (780) is wirelessly coupled with processor (110), such as by a coupling unit (132) or other wireless communication device.

Versions that include a plurality of position sensors located at different positions along the length of a shaft, like position sensors (730, 740, 750, 760, 770) being located at different positions along the length of shaft (700), may be particularly useful in the context of shafts that are operable to bend. This may include shafts that are passively flexible, shafts that are malleable, and shafts that are actively steerable (e.g., based on applied tension from a pull-wire, etc.). An example of a shaving instrument with an actively steerable shaft is described in U.S. Provisional Patent App. No. 62/775,135, entitled "Bi-Directional Articulating Surgical Shaver," filed Dec. 4, 2018, the disclosure of which is incorporated by reference herein in its entirety. Regardless of how the shaft is bent, when the shaft is bent, the plurality of position sensors may provide position data that effectively indicates the bend angle and bend configuration of the shaft. In other words, even when the shaft configuration changes on an ad hoc basis before or during a medical procedure, the plurality of position sensors may still provide accurate position data in real time, allowing processor (110) to drive display (114) to accurately indicate the bent configuration of the shaft, and the location and orientation of an aperture (or other structural features) of the shaft, in real time.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) an elongate shaft defining a longitudinal axis, wherein the elongate shaft includes: (i) a distal end, (ii) an opening, and (iii) a lumen; and (b) a first position sensor, wherein the first position sensor is laterally offset from the longitudinal axis, wherein the first position sensor is fixedly secured relative to the elongate shaft at a known distance from the opening, wherein the first position sensor is configured to generate signals indicating a position of the elongate shaft in three-dimensional space.

Example 2

The apparatus of Example 1, wherein the distal end is closed, wherein the opening is proximal to the distal end.

Example 3

The apparatus of any one or more of Examples 1 through 2, further comprising a cutting element disposed in the lumen, wherein the cutting element is configured to sever tissue protruding through the opening of the elongate shaft.

Example 4

The apparatus of Example 3, wherein the cutting element includes a laterally oriented window with a cutting edge, wherein the opening of the elongate shaft is laterally oriented and includes an edge configured to cooperate with the cutting edge to thereby sever tissue protruding through the opening of the elongate shaft.

Example 5

The apparatus of any one or more of Examples 3 through 4, wherein the cutting element is configured to rotate within the lumen to thereby sever tissue protruding through the opening of the elongate shaft.

Example 6

The apparatus of any one or more of Examples 1 through 5, further comprising a vacuum source in fluid communication with the lumen, wherein the elongate shaft is operable to apply suction from the vacuum source through the opening of the elongate shaft.

Example 7

The apparatus of any one or more of Examples 1 through 6, wherein the first position sensor comprises a wire coil.

Example 8

The apparatus of Example 7, wherein the wire coil is configured to generate an electrical signal in response to an alternating magnetic field, the electrical signal indicating a position of the elongate shaft in three-dimensional space.

Example 9

The apparatus of any one or more of Examples 7 through 8, wherein the wire coil is wound about a first coil axis, wherein the first coil axis is parallel with the longitudinal axis of the elongate shaft.

Example 10

The apparatus of any one or more of Examples 1 through 9, further comprising a second position sensor, wherein the second position sensor is laterally offset from the longitudinal axis, wherein the second position sensor is fixedly secured relative to the elongate shaft at a known distance from the opening, wherein the second position sensor is configured to generate signals indicating a position of the elongate shaft in three-dimensional space.

Example 11

The apparatus of Example 10, wherein the first and second position sensors are angularly offset from each other about the longitudinal axis.

Example 12

The apparatus of Example 11, wherein the first and second position sensors are both located at the same longitudinal position along a length of the elongate shaft.

Example 13

The apparatus of any one or more of Examples 11 through 12, wherein the first position sensor comprises a first wire coil wrapped about a first coil axis, wherein the second position sensor comprises a second wire coil wrapped about a second coil axis.

Example 14

The apparatus of Example 13, wherein the first and second coil axes are parallel with each other.

Example 15

The apparatus of any one or more of Examples 13 through 14, wherein the first and second coil axes are parallel with the longitudinal axis.

Example 16

The apparatus of Example 10, wherein the first position sensor comprises a first wire coil wrapped about a first coil axis, wherein the second position sensor comprises a second wire coil wrapped about a second coil axis, wherein the first coil axis is parallel with the longitudinal axis, wherein the second coil axis is perpendicular to the first coil axis.

Example 17

The apparatus of any one or more of Examples 10 through 15, further comprising a third position sensor, wherein the third position sensor is laterally offset from the longitudinal axis, wherein the third position sensor is fixedly secured relative to the elongate shaft at a known distance from the opening, wherein the third position sensor is configured to generate signals indicating a position of the elongate shaft in three-dimensional space.

Example 18

The apparatus of Example 17, wherein the first, second, and third position sensors are arranged along a helix extending about the longitudinal axis.

Example 19

An apparatus comprising: (a) a first elongate shaft defining a longitudinal axis, wherein the elongate shaft includes: (i) a distal end, and (ii) an opening; (b) a second elongate shaft disposed within the first elongate shaft, wherein the second elongate shaft is rotatable within the first elongate shaft, wherein the second elongate shaft includes a cutting edge, wherein the cutting edge is configured to sever tissue protruding through the opening; and (c) a position sensor, wherein the position sensor is laterally offset from the longitudinal axis, wherein the position sensor is fixedly secured relative to the first elongate shaft at a known distance from the opening, wherein the position sensor is configured to generate signals indicating a position of the first elongate shaft in three-dimensional space.

Example 20

An apparatus comprising: (a) an elongate shaft defining a longitudinal axis, wherein the elongate shaft includes: (i) a distal end, (ii) an opening, and (iii) a lumen; (b) a first position sensor, wherein the first position sensor is laterally offset from the longitudinal axis, wherein the first position sensor is fixedly secured relative to the elongate shaft at a known distance from the opening, wherein the first position sensor is configured to generate signals indicating a position of the elongate shaft in three-dimensional space; and (c) a second position sensor, wherein the second position sensor is laterally offset from the longitudinal axis, wherein the second position sensor is fixedly secured relative to the elongate shaft at a known distance from the opening, wherein the second position sensor is configured to generate signals indicating a position of the elongate shaft in three-dimensional space; wherein the second position sensor is offset from the second position sensor along one or both of a longitudinal dimension or an angular dimension.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein in its entirety.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein in its entirety is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein in its entirety, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) an elongate shaft defining a longitudinal axis, the elongate shaft including:
      (i) a distal end,
      (ii) an opening, and
      (iii) a lumen configured to provide suction to the opening; and
   (b) a first position sensor, the first position sensor being laterally offset from the longitudinal axis, the first position sensor being fixedly secured to the elongate shaft at a first known distance from the opening, the first position sensor being configured to generate signals indicating a position of the elongate shaft in three-dimensional space;
   (c) a second position sensor, the second position sensor being laterally offset from the longitudinal axis and longitudinally offset from the first position sensor, the second position sensor being fixedly secured relative to the elongate shaft at a second known distance from the opening, the second position sensor being configured to generate signals indicating the position of the elongate shaft in three-dimensional space; and
   (d) a third position sensor, the third position sensor being laterally offset from the longitudinal axis, the third position sensor being fixedly secured relative to the elongate shaft at a third known distance from the opening, the third position sensor being configured to generate signals indicating the position of the elongate shaft in three-dimensional space;
   the first, second, and third position sensors being arranged along a helix extending about the longitudinal axis and,
   the first position sensor comprising a first wire coil wrapped about a first coil axis, the second position sensor comprising a second wire coil wrapped about a second coil axis, the first coil axis being parallel with the longitudinal axis, the second coil axis being perpendicular to the first coil axis.

2. The apparatus of claim 1, the distal end being closed, the opening being proximal to the distal end.

3. The apparatus of claim 1, further comprising a cutting element disposed in the lumen, the cutting element being configured to sever tissue protruding through the opening of the elongate shaft.

4. The apparatus of claim 3, the cutting element including a laterally oriented window with a cutting edge, the opening of the elongate shaft being laterally oriented and including an edge configured to cooperate with the cutting edge to thereby sever the tissue protruding through the opening of the elongate shaft.

5. The apparatus of claim 3, the cutting element being configured to rotate within the lumen to thereby sever the tissue protruding through the opening of the elongate shaft.

6. The apparatus of claim 1, further comprising a vacuum source in fluid communication with the lumen, the elongate shaft being operable to apply suction from the vacuum source through the opening of the elongate shaft.

7. The apparatus of claim 1, the wire coil being configured to generate an electrical signal in response to an alternating magnetic field, the electrical signal indicating the position of the elongate shaft in three-dimensional space.

8. The apparatus of claim 1, the first coil axis being parallel with the longitudinal axis of the elongate shaft.

9. The apparatus of claim 1, the second position sensor being in electrical communication with the first position sensor through an electrical node.

10. The apparatus of claim 1, the first and second position sensors being angularly offset from each other about the longitudinal axis.

11. The apparatus of claim 1, the first and second position sensors being both located at the same radial position along a length of the elongate shaft.

12. The apparatus of claim 1, the elongate shaft being operable to bend.

13. An apparatus comprising:
   (a) an elongate shaft defining a longitudinal axis, the elongate shaft including:
      (i) a distal end,
      (ii) an opening, and
      (iii) a lumen;
   (b) a first position sensor, the first position sensor being laterally offset from the longitudinal axis, the first position sensor being fixedly secured relative to the elongate shaft at a first known distance from the opening, the first position sensor being configured to generate signals indicating a position of the elongate shaft in three-dimensional space; and
   (c) a second position sensor, the second position sensor being laterally offset from the longitudinal axis, the second position sensor being fixedly secured relative to the elongate shaft at a second known distance from the opening, the second position sensor being configured to generate signals indicating the position of the elongate shaft in three-dimensional space; the first position sensor being offset from the second position sensor along a longitudinal dimension and an angular dimension;
   (d) a third position sensor, the third position sensor being laterally offset from the longitudinal axis, the third position sensor being fixedly secured relative to the elongate shaft at a third known distance from the opening, the third position sensor being configured to generate signals indicating the position of the elongate shaft in three-dimensional space;
   (e) a handle assembly, the elongate shaft extending distally from the handle assembly, the handle assembly including a memory device configured to store calibration data indicating the first and second known distances;
   the first, second, and third position sensors being arranged along a helix extending about the longitudinal axis and,
   the first position sensor comprising a first wire coil wrapped about a first coil axis, the second position sensor comprising a second wire coil wrapped about a second coil axis, the first coil axis being parallel with the longitudinal axis, the second coil axis being perpendicular to the first coil axis.

* * * * *